United States Patent [19]

Kolhouse et al.

[11] Patent Number: 5,234,905

[45] Date of Patent: Aug. 10, 1993

[54] SOLUBLE CD4 MOLECULES MODIFIED TO PROLONG CIRCULATING HALF-LIFE

[75] Inventors: J. Fred Kolhouse; John C. Deutsch, both of Denver, Colo.

[73] Assignee: University of Colorado Foundation, Inc., Boulder, Colo.

[21] Appl. No.: 669,849

[22] Filed: Feb. 22, 1991

[51] Int. Cl.$^5$ .................. A61K 37/02; C07K 15/14
[52] U.S. Cl. .................. 514/8; 530/350; 530/395; 530/402
[58] Field of Search ............... 530/387, 389, 395, 402, 530/350; 514/8

[56] References Cited

U.S. PATENT DOCUMENTS

| | | | |
|---|---|---|---|
| 4,184,917 | 1/1980 | Dorner et al. | 435/68.1 |
| 4,911,911 | 12/1986 | Casellas et al. | 424/85.91 |
| 5,109,123 | 4/1992 | Reinherz et al. | 435/235.1 |
| 5,116,944 | 5/1992 | Sivam et al. | 530/362 |

FOREIGN PATENT DOCUMENTS

| | | |
|---|---|---|
| 0372752 | 6/1990 | European Pat. Off. |
| 0373896 | 6/1990 | European Pat. Off. |
| 0385909 | 9/1990 | European Pat. Off. |
| 8902922 | 4/1989 | PCT Int'l Appl. |
| 8903222 | 4/1989 | World Int. Prop. O. |
| 9001035 | 2/1990 | World Int. Prop. O. |
| 9005534 | 5/1990 | World Int. Prop. O. |

OTHER PUBLICATIONS

Watanabe, M., (1992), "Chimpanzees Immunized with Recombinant Soluble CD4 Develop Anti-Self CD4 Antibody Responses with Anti-Human Immunodeficiency Virus Activity", Proc. Natl. Acad. Sci. USA, 89:5103–5107.
Gross et al., Eur. J. Biochem., 173:653–659, (1988), "Involvement of Various Organs in the Initial Plasma Clearance of Differently Glycosylated Rat Liver Secretory Proteins".
Peterson et al., (1988), Cell, 54:65–72.
Schooley et al., (1990), Ann. Int. Med., 112:247–253.
Larsen et al., (1989), Blood, 73:1842–1850.
Roth et al., (1965), Anal. Biochem., 10:35–52.
Schiff et al., (1986), Hepatology, 6:837–847.
Morell et al., (1971), J. Biol. Chem., 246:1461–1467.
Morell et al., (1968), J. Biol. Chem., 243:155–159.
Ashwell et al., (1982), Ann. Rev. Biochem., 51:531–554.
Fukuda et al., (1989), Blood, 73:84–89.
Hussey et al., (1988), Nature, 331:78–81.
Chao et al., (1989), J. Biol. Chem., 264:5812–5817.
Maddon et al., (1985), Cell, 42:93–104.
Morell et al., (1966), J. Biol. Chem., 241:3745–3749.
van den Hamer et al., (1970), J. Biol. Chem., 245:4397–4402.
Pyatak, (1980), Res. Comm. Chem. Path. Pharm., 29:113–127.
Fahey et al., "Status of Immune-based Therapies in HIV . . . ", Clin. Exp. Immunol., 88:1–5, Apr. 1992.
S. Yu et al., Archives of Biochemistry and Biophysics, 179:477–485, 1977.
K.-J. Kao et al., Journal of Biological Chemistry, 255:10134–10139, 1980.
J. M. Sodetz et al., Journal of Biological Chemistry, 252:5538–5546, 1977.
Carr et al., J. Biol. Chem., 264:21286–21295, Dec. 15, 1989.

Primary Examiner—Robert A. Wax
Assistant Examiner—Stephen Walsh
Attorney, Agent, or Firm—Greenlee & Winner

[57] ABSTRACT

A method for extending soluble CD4 serum half-life in mammals is described. The method comprises modifying soluble CD4 glycosylation so as to inhibit clearance from serum. In a preferred embodiment, clearance by hepatocyte galactose receptors is inhibited by removal of soluble CD4 terminal sialic residues followed by oxidation of exposed galactose residues. The modified soluble CD4 molecules are demonstrated to possess extended serum half-life.

8 Claims, No Drawings

SOLUBLE CD4 MOLECULES MODIFIED TO PROLONG CIRCULATING HALF-LIFE

The United States government may have certain rights in this invention. This invention was made, in part, with funding from the National Institutes of Health.

FIELD OF THE INVENTION

This application relates to compositions for antiviral or other therapy and to methods for glycoprotein structural modifications which prolong the half-life of those proteins in the circulation by blocking specific liver clearance mechanisms. Specifically, this application relates to compositions useful in the treatment of Human Immunodeficiency Virus (HIV) infections.

BACKGROUND OF THE INVENTION

The primary immunologic abnormality in HIV-infected patients with an infection in the active stage is the progressive depletion and functional impairment of T lymphocytes expressing the CD4 cell surface glycoprotein (Lane et al. (1985) Ann. Rev. Immunol. 3:477). Generally, T lymphocytes expressing the CD4 surface glycoprotein have a helper/inducer T cell phenotype (Reinherz et al. (1980) Cell 19:821), but such T cells can also have cytotoxic/suppressor activity (Thomas et al. (1981) J. Exp. Med. 154:459). It is believed that the loss of the helper/inducer functions in immunocompromised AIDS or ARC patients leads to the opportunistic infections and malignancies associated with AIDS.

Molecular studies of HIV infection of T cells have shown that HIV specifically and selectively infects T cells expressing CD4. It was also observed that CD4-specific monoclonal antibodies could block HIV infection and syncytia formation (Dalgeish et al. (1984) Nature 312:767; McDougal et al. (1985) J. Immunol. 135:3151). Maddon et al. (1986) Cell 47:333 showed that cells normally non-permissive for HIV infection which expressed a stable cDNA encoding CD4 became permissive for HIV infection. These results showed that CD4 was required for HIV infection. McDougal et al. (1986) Science 231:382, demonstrated complex formation between CD4 and gp120, the major HIV envelope glycoprotein.

cDNA encoding CD4 has been cloned and sequenced (Maddon et al. (1985) Cell 42:93). Sequence analysis shows an N-terminal signal peptide sequence, domains which exhibit homology to certain immunoglobulin variable-region domains, potential glycosylation sites at about 273 and about 303 in the amino acid sequence, a potential trans-membrane domain from about 375 to about 395, and a potential cytoplasmic domain extending through the C-terminus of the protein. Peterson and Seed (1988) Cell 54:65 performed site-directed mutagenesis of the CD4 protein to determine HIV binding sites, and correlated this information with epitopes recognized by CD4-specific monoclonal antibodies. Amino acid substitutions in the region of amino acids 45–47 of the protein appeared to destroy both HIV binding and syncytium formation.

Secreted, soluble forms of CD4 have been synthesized using truncated coding sequences. CD4 derivatives of about 370 amino acids have been produced; these are glycosylated when produced in appropriate host cells. Such molecules bind HIV gp120 effectively and can block HIV infection of susceptible cells (See, e.g., Smith et al. (1987) Science 238:1704; Fisher et al. (1988) Nature 331:76; and Hussey et al. (1988) Nature 331:78). Soluble truncated CD4 proteins as short as 113 amino acids, which are not glycosylated, can block HIV-mediated cell fusion (Chao et al. (1989) J. Biol. Chem. 264:5812). Thus it is clear that intact oligosaccharide side chains are not required for HIV binding or for cell fusion events.

The use of soluble forms of CD4 has been proposed for AIDS treatment or prophylaxis (See e.g., EP 0 385,909, published Sep. 5, 1990). Soluble forms of CD4 are known to have a short half-life in circulation in relation to certain serum proteins. Because the in vivo plasma half-life of soluble CD4 has been shown to be relatively short, various strategies have been employed to stabilize the protein against clearance. (See, e.g., WO 89/03222; WO 89/02922; WO 90/01035; and WO 90/05534). Conjugates have been prepared in which polyethylene glycol or other hydrophilic polymers are attached to the CD4 either via amino acid free functional groups or via sugar moieties in the oligosaccharide side chains of the glycosylated soluble CD4 protein. A second approach to stabilizing the CD4 protein in circulation has been to produce fusion proteins including a soluble CD4 portion and a portion from a protein of long circulating half-life, such as an immunoglobulin. Such fusions exhibited longer plasma half-lives in animal models than sCD4 without added domains.

Therapeutic proteins may be removed from circulation by a number of routes. For some pharmacologically active proteins, there are specific receptors which mediate removal from circulation. Proteins which are glycosylated may be cleared by lectin-like receptors in the liver, which exhibit specificity only for the carbohydrate portion of those molecules. Nonspecific clearance by the kidney of proteins and peptides (particularly nonglycosylated proteins and peptides) below about 50 kDa has also been documented. It has been noted that asialo-glycoproteins are cleared more quickly by liver than native glycoproteins or proteins lacking glycosylation (Bocci (1990) Advanced Drug Delivery Reviews 4:149). The sialic acid residues of erythropoietin appear to contribute to its stable circulation (Fukuda et al. (1989) Blood 73:84). In contrast, studies of tissue-type plasminogen activator (tPA) showed that the oligosaccharide sidechains were not the primary determinants for clearance from solution, but rather rapid clearance was dependent on the amino acid sequence within one or more domains of the molecule. The presence and type of glycosylation made a secondary, less significant contribution to clearance (Larsen et al. (1989) Blood 73:1842).

Mammalian glycoproteins often have N-acetylneuraminic acid (sialic acid) as the external (terminal) residue of the oligosaccharide chains which may be N-linked or O-linked (See, e.g., Osawa and Tsuji (1987) Ann. Rev. Biochem. 56:21).

Where the nature of the oligosaccharide is the primary determinant for clearance from circulation, generally glycoproteins with terminal sialic acid residues removed (asialoglycoproteins) are cleared more quickly than their intact counterparts. Circulating glycoproteins are exposed to sialidase(s) (or neuraminidase) which can remove terminal sialic acid residues. Typically the removal of the sialic acid exposes galactose residues, and these residues are recognized and bound by galactose-specific receptors in hepatocytes (reviewed in Ashwell and Harford (1982) Ann. Rev. Biochem. 51:531). Liver also contains other sugar-specific receptors which mediate removal of glycoproteins from circulation. Specificities of such receptors also include N-acetylglucosamine, mannose, fucose and phosphomannose. Glycoproteins cleared by the galactose receptors of hepatocytes undergo substantial degradation and then enter the bile; glycoproteins cleared by the mannose receptor of Kupffer cells enter the reticuloendothelial system (reviewed in Ashwell and Harford (1982) Ann. Rev. Biochem. 51:53).

Studies with asialo-ceruloplasmin and derivatives showed that asialo-ceruloplasmin in which galactose residues were oxidized by treatment with galactose oxidase and horseradish peroxidase and asialoagalacto-ceruloplasmin exhibited extended circulating half-lives as compared with asialo-ceruloplasmin (Morell et al. (1968) J. Biol. Chem. 243:155). Efficient removal by the galactose receptor appears to require at least two exposed galactose residues. In contrast, transferrin is a glycoprotein in which the sialylation state of the oligosaccharide is not key to rapid clearance from circulation (Morell et al. (1971) J. Biol. Chem. 246:1461).

From the foregoing cited examples of glycoproteins for which sialylation is the key determinant of clearance from circulation and those for which sialylation has no bearing on clearance or for which oligosaccharides play a relatively insignificant role in clearance, one may conclude that the fate of a particular glycoprotein in circulation and its apparent mechanism for clearance must be determined empirically. Similarly, strategies for prolonging the circulation of a particular glycoprotein must be evaluated on a case-by-case basis. The mechanism for clearance must be evaluated and the strategies for slowing or avoiding clearance must take into account maintenance of desired biological activity or function, potential toxicity, potential immunogenicity and cost.

A problem solved by the present invention is the prolongation of the circulating half-life of soluble CD4 derivatives, thus reducing the quantity of injected material and frequency of injection required for maintenance of therapeutically effective levels of circulating sCD4 for treatment or prophylaxis of HIV-infected individuals. The short in vivo plasma half-life of sCD4 is undesirable from the standpoint of the frequency and the amount of soluble CD4 protein which would be required in the prophylaxis or treatment of AIDS. The present invention provides means to prolong the circulating half-life of sCD4 with the most conservative but still effective change to the glycoprotein structure and with the substantial maintenance of gp120 binding activity.

SUMMARY OF THE INVENTION

It is an object of this invention to provide a means for stabilizing glycoproteins in circulation when the glycosylation of that protein provides the primary determinant for clearance. Increased half-life is achieved in such glycoproteins by treatments which block or inhibit removal of the protein by sugar-specific receptor, such as the galactose and mannose receptors in the liver. In particular, the prolonging of soluble CD4 derivatives in circulation is described. Prolonged circulating half-lives are desirable in therapeutic proteins because frequency and/or size of dose can be reduced when half-life is longer.

It is also an object of this invention to provide a modified soluble CD4 derivative with increased plasma half-life as compared with the unmodified derivative. Increased half-life of sCD4 is achieved in general by means which block or inhibit removal of sCD4 by galactose, mannose or other sugar-specific receptors. More specifically, means are provided for modification of terminal galactose or mannose residues of glycosylated sCD4 or its derivatives such that removal by sugar-specific receptors in the liver is inhibited or prevented. Modifications that result in increased half-life include, but are not limited to, exposure of galactose residues followed by oxidation or derivatization of the galactose such that binding of the modified sCD4 to galactose receptor is inhibited or blocked. A preferred embodiment is one in which the terminal sialic acid residues of the oligosaccharide side chains of the soluble CD4 or soluble CD4 derivative have been removed with neuraminidase treatment, and then the exposed galactose residues are oxidized by galactose oxidase and horseradish peroxidase treatment. The oxidation of the exposed galactose residues has the effect of preventing rapid clearance of the modified CD4 from circulation by specific galactose receptors in the liver. It is understood that other structural modifications of terminal galactose residues, including but not limited to addition of a functional group or small molecule or mild oxidation treatment, which have the effect of blocking, inhibiting or preventing recognition of terminal galactose residues without destroying the HIV gp120-binding activity are functionally equivalent. It is also contemplated that structural modification of one or more sialic acid residues of oligosaccharide portions of a soluble CD4 molecule may be made with the result that terminal sialic acid residues are not removed by neuraminidase; as a result the persistence of the modified sCD4 in circulation is increased. This invention also encompasses the modification of terminal mannose residues so as to inhibit or prevent clearance via the mannose receptor of liver.

Furthermore, a modified sCD4 may be prepared in which sialic acid (e.g., with neuraminidase) and galactose residues (e.g., with galactosidase) are removed to expose mannose residues. Those exposed mannose residues may be structurally altered by the addition of a functional group or small molecule or by mild oxidation treatment, with the result that recognition of this modified sCD4 by the mannose receptor and removal from circulation of liver is prevented or inhibited. For all modified sCD4 molecules, solubility in pharmacological and physiological fluids must be maintained and the biological activity of HIV gp120/160 binding must likewise be maintained.

An object of this invention is a therapeutic composition comprising a concentration of a modified sCD4 effective for binding HIV gp120/gp160 and a pharmaceutically acceptable carrier. Preferably, the half-life in human circulation of said modified sCD4 is greater than about 24 hours. A preferred sCD4 is one which has been treated to remove sufficient sialic acid to expose at least two galactose residues and which has been further treated, e.g., with galactose oxidase and horseradish peroxidase so that clearance of the modified sCD4 from circulation by the galactose-specific receptor of liver is inhibited or prevented.

A further object of the invention is as method for increasing the half-life of a glycoprotein in circulation in a mammal, where the glycoprotein is normally cleared from circulation by the galactose receptor of liver when in an asialo-glycoprotein form. The method comprises the steps of treating said glycoprotein to remove terminal sialic acid residues to produce an asialo-glycoprotein, and oxidizing any galactose residues of said asialo-glycoprotein to produce an oxidized asialo-glycoprotein, whereby removal of said oxidized asialo-glycoprotein by the galactose receptor of liver is inhibited. In a preferred embodiment which specifically exemplifies the prolonging of sCD4 in circulation, sialic acid residues are removed by neuraminidase treatment and the galactose residues are oxidized by treatment with galactose oxidase and horseradish peroxidase.

In principle, the teachings for the structural modification of sCD4 to prolong circulating half-life can be applied to any pharmacologically active protein for which a longer circulating half-life is advantageous, in which intact oligosaccharide chains are not required for the desired biological activity, and for which the oligosaccharide carries the signal of primary importance for clearance from the bloodstream.

DETAILED DESCRIPTION OF THE INVENTION

CD4, as defined herein, is the full-length CD4 polypeptide having the biological activities of native human CD4. Amino acid sequence variations and derivatizations which allow the maintenance of the biological activities of the CD4 protein are included within the definition. Native, CD4, and recombinant CD4 which is synthesized in recombinant eukaryotic cells is a glycoprotein. Maddon et al. (1985), supra, notes that there are two sites for N-linked glycosylation, at about 275 and at about 305. EP 372 752 gives the sugar content of a CD4 molecule, but the exact structure of the oligosaccharide chain(s) is not known. However, it is generally understood in the art that sialic acid (N-acetylneuraminic acid) residues will be terminal in the oligosaccharide side chain of a mature glycoprotein synthesized in a mammalian cell, and that galactose residues will be exposed when sialic acid is absent or removed (See, e.g., Osawa and Tsuji (1987) supra). The art knows that exact oligosaccharide structure of a glycoprotein may vary with respect to sugars present, the glycosylation enzymes present and the relative proportions of each according to the choice of the particular eukaryotic cell in which the recombinant CD4 (or soluble CD4) is synthesized.

As defined herein soluble CD4 (sCD4) is a variant of the CD4 protein which is soluble in water-based pharmaceutical preparations (or pharmaceutically acceptable solvents or compositions which include components in addition to water) and in physiological fluids, including plasma, at a level which is sufficient to achieve a therapeutically effective concentration in circulation. sCD4 proteins include those in which part or all of the transmembrane domain of the primary structure of CD4 has been deleted, for example through truncation of the coding sequence; the cytoplasmic domain of the protein may likewise be deleted without the loss of the desired biological activity of HIV gp120 binding. sCD4 molecules capable of being glycosylated when synthesized in appropriate host cells are described in Smith et al. (1987), supra; Fisher et al. (1988), supra, Hussey et al. (1988), supra; EP Publication No. 385 909, supra; Deen et al. (1988) Nature 331:82–84; all of which are incorporated by reference herein. Unless otherwise noted and like the native full-length CD4, the sCD4 molecule is glycosylated. In any case, the HIV gp120 binding activity of the native CD4 is substantially maintained in the soluble CD4 derivative and modified sCD4 of the present invention. Peterson and Seed (1988), supra, e.g., address the issue of amino acid substitutions and deletions in the N-terminal region of the CD4 and the effects on gp120 binding. It is believed that some form of glycosylation is necessary for protection of sCD4 from degradation in circulation and/or clearance by the kidneys. Thus, sCD4 of the present invention must retain some level of glycosylation: preferably the minimal structural modification of the glycosylation is made which acts to prolong circulating half-life.

For the purposes of monitoring sCD4 molecules or derivatives in an animal model (e.g., in the rat, as described in the Examples), radio-iodinated sCD4 is prepared using, e.g., Bolton-Hunger reagent and instructions for use from Nuclear England Nuclear (Boston, Mass.), or according to any other technique well-known to the art.

Modified sCD4 molecules of the present invention are those with structural alterations (modifications) of the oligosaccharide portions of the glycoprotein which result in prolonged circulating half-life by blocking or inhibiting clearance via sugar-specific receptors of the liver. Preferably the sCD4 glycoproteins are synthesized in a recombinant mammalian host. The chemical and/or enzymatic treatments to produce the structural modifications of the oligosaccharide should not substantially alter the binding reaction of sCD4 with the HIV target protein. It is preferred that the circulating half-life of a modified sCD4 of the present invention be at least about 24–48 hours in humans (or at least about 6–12 hours as measured in a rat animal model). It is most preferable that the structural modification of the oligosaccharide so as to prolong circulating half-life is the most conservative structural change which will achieve this end. A variety of chemical derivatization procedures, or chemical and/or enzymatic procedures, as understood in the art, may be employed to produce the modified sCD4 molecules of the present invention. The modified sCD4 specifically exemplified in the present invention is oxidized asialo-sCD4, in which the terminal galactose residues have been oxidized by treatment with galactose oxidase and horseradish peroxidase. As for full-length CD4, there may be variations in amino acid sequence so long as glycosylation and gp120 binding activity are maintained.

Asialo-sCD4 is a modification of the sCD4 in which the sialic acid residues are wholly or partially absent from the oligosaccharide portion of the molecule so that at least two terminal galactose residues are exposed. Sialic acid residues may be removed by sialidase or neuraminidase treatment; asialo-sCD4 may also be produced by synthesizing sCD4 in a host cell which is unable to add the terminal sialic acid residues during oligosaccharide synthesis. Most preferably, at least two galactose residues are exposed.

Agalacto-asialo-sCD4 is a sCD4 derivative in which terminal sialic acid and galactose residues are absent, either as a result of enzymatic or chemical removal or through synthesis of the sCD4 in a host cell which is deficient in sialic acid and galactose addition. Where galactose residues are terminal in the oligosaccharide portion of a glycoprotein, those galactose residues may be removed with $\beta$-galactosidase.

Oxidized asialo-sCD4 is an asialo-sCD4 derivative in which the galactose residues have been oxidized by mild oxidation conditions, for example with galactose oxidase and horseradish peroxidase. Although not wishing to be bound by any particular mechanism, it is believed that such treatment oxidizes the C6 position of the galactose and prevents recognition and removal of the molecule from circulation by the galactose receptor of the liver; thus prolonging the half-life of the modified sCD4 in circulation so that said molecule, either injected alone or in conjunction with any other HIV treatment, is therapeutically effective. Mild oxidation conditions include any chemical or enzymatic oxidation which oxidizes the terminal sugar residue without substantial effect on the gp120 binding function of the sCD4 protein or any protective function of glycosylation on the protein.

Other structural modifications of the oligosaccharide portion of a sCD4 molecule which prolong the circulating half-life by preventing and/or inhibiting removal of sCD4 by the galactose or mannose receptors are within the scope of the invention. While the experimental results described in this specification are consistent with the model for the clearance of asialo-sCD4 from circulation by the hepatocyte galactose receptor, Applicants do not want to be bound by this model. It is understood that other mechanisms may contribute to clearance. It is likely that treatment of the asialo-sCD4 with galactose oxidase and horseradish peroxidase prevented binding of terminal sugar residues by the galactose receptor. Such modifications can include the structural modification of sialic acid of the glycoprotein so that neuraminidases cannot remove the terminal sialic acid residues to expose the galactose residues which could then mediate clearance by virtue of their recognition by the galactose specific receptor of liver. An asialo-sCD4 can be modified by the addition of functional groups to the galactose so that recognition and removal from circulation by the galactose receptor is prevented or inhibited. Chemical modification or derivatization of the C6 position of galactose is preferred to maximize half-life and minimize clearance without significantly affecting gp120 binding function and without eliciting negative physiological reactions; minimal and mild treatment is preferred. Functional groups or other structure-modifying molecules in this invention to be added to the oligosaccharide portion of an sCD4 exclude any polymeric substituents. Also contemplated are analogous structural changes to terminal mannose residues of asialoagalacto-sCD4 which will inhibit or prevent clearance from circulation via the mannose receptor of Kupffer cells of the liver. The binding of modified sCD4 molecules to gp120 will not be affected by the structural modifications to the oligosaccharide portion of the molecule.

For any modified sCD4 molecule of the present invention it is most desirable that an immunological response will not be elicited in a human patient exposed to the modified sCD4. It is also required that the HIV gp120 binding activity is not significantly decreased to detrimentally affect the therapeutic function of sCD4 by the structural modification employed to confer prolonged circulation. It is also most desirable that any structural modification of a sCD4 molecule does not result in toxicity in a patient to which that modified sCD4 is administered. Clearly for use in therapeutics, the modified sCD4 should have minimal toxic, irritant or other side effects on administration to humans. The ability of a modified sCD4 molecule to bind HIV gp120 can be determined using a test such as that described in EP 372 752, published Jun. 13, 1990, which document is incorporated by reference herein.

The circulating half-life of a protein (or glycoprotein) is the time for the initial blood concentration of that protein to fall to half the initial concentration.

As it relates to the modified sCD4 molecules of the present invention, the term biological activity refers to the ability of the sCD4-related molecule to bind the HIV gp120 (or gp160) with substantially the same affinity as the unmodified sCD4 molecule. Modifications which substantially decrease the biological activity of sCD4 are to be avoided. Once the modified sCD4 has bound the HIV gp120, the bound HIV cannot infect a susceptible cell, thus preventing the spread of viral infection. Similarly, an HIV-infected cell expressing gp120 on its surface and where gp120 is bound to an sCD4 molecule, cannot participate in syncytium formation with a cell expressing CD4 on its surface. The inhibition of syncytium formation further contributes to the therapeutic effect of an sCD4-related protein in an HIV-infected individual. Bound complexes of modified sCD4 with HIV via gp120 or with a patient's cells via surface gp120 may also be targeted for removal from the circulation, for example, using an extracorporeal device with means for removal of sCD4-gp120 complexes, either associated with viral particles or with cells in circulation. Similarly, HIV particles or HIV-infected cells may be targeted for destruction via bound modified sCD4 molecules.

The modified sCD4 molecules of this invention may be purified by any means known to the art before formation into therapeutic compositions. Therapeutic compositions are formulated using a modified sCD4 with a prolonged circulating half-life and a physiologically acceptable carrier; such compositions can be sterilized by any means known to the art which does not significantly alter either the desired biological activity or the prolonged half-life in circulation. In addition, the modified sCD4 molecules of the present invention may be used in conjunction with other compositions useful in the treatment or prophylaxis of AIDS in HIV-infected individuals. Such other compositions include, but are not limited to, AZT, DDC, DDI, neutralizing antibodies, immunocytotoxins, gp120 fragments and HIV vaccine preparations.

For glycoproteins other than sCD4 for which a derivative with prolonged circulating half-life is desired, the skilled artisan can apply the teachings of this disclosure. In a rat model system, as described herein, the artisan can determine whether the galactose receptor is the primary means of clearance by preparing a radiolabeled, desialylated derivative, testing for bile excretion and also for competition by asialofetuin of liver-associated counts. Inhibition of clearance with co-injection of asialofetuin and appearance of asialoglycoprotein-associated radioactivity indicates clearance by the liver galactose receptor. Then, for example, the glycoprotein of interest can be desialylated, preferably oxidized under mile conditions, e.g., with galactose oxidase and horseradish peroxidase, and prolonged half-life can be confirmed in the animal model as described herein. Analogous appropriate tests and treatments will be readily apparent to the skilled artisan when clearance by another sugar receptor is the mode of clearance. For any glycoprotein in which sialic acid residues are normally present, treatment with sialotransferase under appropriate conditions to ensure complete sialylation will also prolong circulating half-life.

In principle, the teachings presented herein may be applied to any sCD4 modified to improve circulating half-life and/or HIV gp120/gp160 binding in such a way that glycosylation during synthesis is not prevented. Furthermore, mixtures of sCD4-related molecules and modified sCD4 molecules may be combined in a therapeutic composition useful for prophylaxis or treatment of HIV infection and/or for alleviation of the detrimental effects of HIV infection. A uniform modified glycoprotein may be incorporated in a therapeutic composition or a mixture of modified glycoprotein may be formulated in such a composition, so long as the desired therapeutic action is achieved by those molecules and so long as clearance by sugar-specific receptors mediating clearance is inhibited or prevented by the modification or modifications made to said glycoprotein. This methodology is applicable to therapeutic sCD4 molecules or to other therapeutically useful glycoproteins which are cleared from circulation by sugar-specific receptors.

It will be readily apparent to those of ordinary skill in the art that assays, reagents, procedures and techniques other than those specifically described herein, can be employed to obtain the same or equivalent results and achieve the goals described herein. For example, chemical means of oxidation or removal of sialic acid can be readily substituted for enzymatic means specifically described. All such alternatives are encompassed by the spirit and scope of this invention.

EXAMPLE 1

Fate of Circulating Soluble CD4

This example describes the elucidation of the clearance mechanism for circulating recombinant soluble CD4 (sCD4) in the rat animal model. The recombinant sCD4 used herein is the product of a truncated coding sequence of CD4. The terms [$^{125}$-I]-sCD4 and sCD4 are used interchangeably but only radiolabelled sCD4 was used in these experiments. The [$^{125}$I]-sCD4 used in the experiments described herein was obtained from Biogen, Cambridge, Mass., and was stored at $-70°$ C. prior to use. The radioactive sCD4 used in these experiments had a specific activity of about 10 microcuries per microgram of protein.

The rat is the model animal system used to study sCD4 clearance from circulation. The studies are performed using the following general scheme.

Rats are fasted overnight and then weighed before a clearance experiment is begun. Then each rat is anaesthetized by intraperitoneal injection of an appropriate amount of an aesthetic, e.g., 5.2 mg sodium pentobarbital per 100 g body weight.

sCD4 is prepared for injection by preparing 0.15M sodium chloride (NS) to which 1 mg bovine serum album (BSA) is added.

Then [$^{125}$I]-sCD4 is added, preferably about 100,000 cpm as measured in a gamma counter. It is necessary to add sCD4 to solutions already containing BSA and to pretreat equipment with BSA because otherwise the sCD4 tends to adhere to the walls of test tubes, pipet tips, etc. The use of BSA as a carrier protein tends to reduce the amount of sCD4-radioactivity adhering to tubes, etc.

The sCD4 sample is drawn up into a BSA-coated 1 cc syringe, and a second syringe is prepared with 1 ml NS containing 1 mg/ml BSA to flush the IV tubing after sCD4 injection. A peristaltic pump and tubing are prepared with 0.15M NaCl.

When the rat is thoroughly anaesthetized, the peritoneum is opened and the abdominal cavity is exposed with a 2.5 inch vertical cut. The are is flushed with 0.15M NaCl and covered with an NS-soaked gauze sponge which is kept moist throughout the experiment. An IV is secured in the tail. The sample is injected and the IV tubing is then flushed with NS. Timing is started half-way through the 1 ml NS flush. A NS flush continues at 7 ml/h throughout the course of the experiment. The peristaltic pump is stopped at the end of the experiment. For long term experiments, the sample and the 1 ml flush are administered under anesthesia without opening the peritoneal cavity. At the end of a long-term (greater than 2 hr) experiments, the animal is again anesthetized, and the peritoneal cavity is opened, the portal vessels are ligated with suture and the animal is exsanguinated by intracardiac puncture, simultaneously collecting blood in a measured volume that is placed in vials containing EDTA as anticoagulant. In all cases, the portal vessels were ligated after opening the peritoneal cavity, and this ligation signals the end of the experiment.

To collect a blood sample, the heart is pierced and about 5 ml blood is collected. A measured volume is placed in a glass counting vial before the blood clots and radioactivity is determined by gamma counting.

The liver is removed immediately after the blood sample is taken if a liver sample is desired. The hepatic portal vein is sutured before the liver is actually removed. The liver is rinsed in distilled water, blotted, weighed and placed in a glass counting vial. If desired, spleen, kidneys, intestine can be removed, rinsed, blotted and counted in a gamma counter.

All glassware, tubing, pipets, etc. are also counted.

For determination of [$^{125}$I]-sCD4-related counts appearing in the bile, the bile duct is cannulated and means for collecting bile are prepared in the rat before the sCD4 sample is injected.

To look at clearance, rats were injected with sCD4 with or without infusion of either the glycoprotein fetuin or asialofetuin. At the noted times after injection of the sCD4, rats were sacrificed and the radioactivity in the blood samples and in livers was determined. Table 1 summarizes the results of this experiment. The asialofetuin infusion resulted in about a 46% increase in blood-associated sCD4 radioactivity.

These results suggested that there might be heterogeneity in the [$^{125}$I]-sCD4 molecules. The relative increase in radioactivity in the bloodstream at 10 min after injection with sCD4 and asialofetuin as compared with injection of sCD4 alone or injection of sCD4 and fetuin suggests that a major mode of clearance is the galactose receptor in hepatocytes. It is proposed that sCD4 molecules with complete sialylation had a long half-life and that those with uncovered galactose residues have a short half-life in circulation.

EXAMPLE 2

Preparation of Control and Asialo-sCD4

To further study the mechanism for clearance of sCD4, a desialylated preparation of [$^{125}$-I]-sCD4 was made for comparison with an untreated control preparation.

10 microliters of [$^{125}$I]-sCD4 containing about 0.2 ug protein was added to 2.2 ml 0.1M sodium acetate (pH 4.5) containing 1 mg/ml BSA. 1 ml of this mixture was transferred to each of two 15 ml conical centrifuge tubes and 1 ml 0.1M sodium acetate was added to each. Then a 20 microliter aliquot of neuraminidase Type V (Sigma Chemical Co., St. Louis, Mo.) (about 0.1 units) was added to one of the tubes, and the other served as an untreated control. From this point on in the preparation, the tubes were treated in parallel. Both tubes were incubated at 37° C. for 2 hr. Each mixture was then dialyzed using tubing with an exclusion limit of 12,000–14,000 d against 1 liter TC-PBS buffer overnight at 4° C. TC-PBS contains 6.5 mM sodium phosphate, 3.5 mM potassium phosphate, 0.14M sodium chloride (pH 7.40). The dialysates were then collected, stored at 4° C., and the radioactivity in aliquots of each were determined by liquid scintillation counting (10 microliters of control sCD4=21325; 10 microliters of asialo-sCD4=19490 cpm). Treatment of the sCD4 with neuraminidase yielded substantially desialylated sCD4 (asialo-sCD4). The control sample was assumed to be fully sialylated sCD4.

In some experiments a second neuraminidase treatment followed that described above. After the first two hour incubation, an additional 200 microliters neuraminidase (1 unit) was added and incubation was continued an additional two hours at 37° C.

To determine the radioactivity associated with relatively high molecular weight material, aliquots of the asialo-sCD4 and of the control sCD4 were precipitated with trichloroacetic acid as follows: 10 microliters of BSA (1 mg) was added to a borosilicate tube (5 ml size) and then a 890 microliter aliquot of dialyzed sCD4 and TC-PBS was added. After mixing, 100 microliters of cold 100% TCA was added, the samples were mixed and held on ice for 10 min. Then each tube was centrifuged for 10 min. 500 microliter supernatant samples, pellets, and the syringe used to measure the sample were then counted.

Rats R11 and R14 were injected with asialo-CD4 (twice digested with neuraminidase). It appears that the neuraminidase treatment to remove terminal sialic acid residues results in a significant relative increase in liver-associated radioactivity and a substantial relative decrease in bloodstream-associated radioactivity at 10 min post-injection. The results in Tables 1 and 2 suggest that circulating sCD4 is removed by the galactose receptor of the liver. The results also suggest some heterogeneity in the sCD4 preparation with respect to sialylation levels of the recombinant sCD4.

To attempt to lengthen the circulating lifetime of sCD4 by preventing recognition and binding of asialo-sCD4 by the hepatocyte galactose receptor, asialo-sCD4 was treated with galactose oxidase and horseradish peroxidase to oxidize the carbinol residues of galactose residues to aldehydes. It was found necessary to incorporate protease inhibitors in the oxidation reaction mixtures. The oxidations were performed as follows:

Galactose oxidase (Sigma Chemical Co., St. Louis, Mo.) was diluted to 0.5 units/ml in 0.1M sodium phosphate (pH 7.0). Horseradish peroxidase (Sigma Chemical Co., St. Louis, Mo.) was diluted to 0.5 units/microliter in 0.1M sodium phosphate (pH 7.0). Digestions were performed in 0.15M sodium chloride, 45 mM sodium acetate, 20 mM sodium phosphate (pH 7.0). The final quantities of galactose oxidase and horseradish peroxidase were 15 units per oxidation reaction and 20 units per oxidation reaction, respectively. All glassware, pipets, etc. were precoated with a 1 mg/ml solution of BSA. A reaction volume of 1.0 ml contained 150 microliters of asialo-sCD4 (about 0.5 ug), 30 microliters (0.15 units) galactose oxidase, 20 units horseradish peroxidase, and 1 mg BSA. The following protease inhibitors were added to the oxidation reactions as follows: 20 microliters 0.1M phenylmethylsulfonyl fluoride in toluene, 20 microliters 0.1M 1,10-phenanthroline, 4 microliters 0.5M iodoacetamide in water. Control reactions included one without GO and HPO, and one without asialo-sCD4. Reactions were carried out in 15 ml conical centrifuge tubes precoated with BSA. After incubation for 66 hr at 25° C., reaction mixtures were individually dialyzed to remove low molecular weight reaction products, toluene, etc. and to adjust the buffer environment to tissue culture-PBS. Immediately before injection, the control asialo-sCD4 sample was prepared by combining the two control reaction tubes; thus the control asialo-sCD4 was exposed to GO and HPO for no more than about 1 min. Analysis of the reaction products showed that there was insignificant proteolytic activity in the enzyme preparations if the above-noted protease inhibitors were included.

Rats were injected with oxidized asialo-sCD4 and control asialo-sCD4. Radioactivity in liver and blood samples was determined at intervals after injection. The results are summarized in Table 3. At 20 min post-injection, there was approximately five-fold more label in the bloodstream for the asialo-sCD4 treated with GO and HPO as compared with control asialo-sCD4. The persistence of the oxidized asialo-sCD4 in circulation was clearly greater than that of asialo-sCD4 or sCD4 (See, e.g., Tables 1 and 3).

The appearance of [$^{125}$I]-label in the bile was monitored in one rat injected with sCD4 and one injected with GO/HPO oxidized asialo-sCD4. Bile samples were collected at 15 min intervals over 2 hr post-injection and radioactivity was measured in each. The results are presented in Table 4. Over seven times as many [$^{125}$I]-sCD4-associated counts as [$^{125}$I]-oxidized asialo-sCD4 enter the bile within the first two hours post-injection. The relative radioactivity associated with liver and bile is nearly twice as great for injection of the intact sCD4 as for the injection of oxidized asialo-sCD4. Thus, the oxidation of the galactose moieties of asialo-sCD4 appears to interfere with clearance from the bloodstream by hepatocytes. The results obtained in the foregoing experiments are consistent with clearance of asialo-sCD4 by the galactose receptor in hepatocytes.

The estimated half-life of sCD4 in the circulation of rat is less than 15 min, at least in the early phase of clearance. The estimated half-life of asialo-sCD4 is less than 5 min; clearance is linear. In contrast, the estimated half-life in circulation for oxidized asialo-sCD4 is greater than 6 hrs. Thus, treatment of asialo-sCD4 with galactose oxidase and horseradish peroxidase dramatically increases circulating half-life.

Deglycosylated sCD4 was prepared to determine the effect of removal of the oligosaccharide side chains from the sCD4 proteins on circulating half-life and to determine the route of clearance of the sCD4 polypeptide from the bloodstream. 500 microliters of asialo-sCD4 was mixed with 4.2 microliter of Endoglycosidase F in 5mM EDTA 50% glycerol (New England Nuclear, Boston, Mass.), 12.5 microliters of 0.2M EDTA and double distilled water to 1 ml. The corresponding control was identical except that 4.2 microliters of 5 mM EDTA in 50% glycerol was substituted for the endoglycosidase F. All tubes, dialysis tubing, pipet tips, etc. were precoated with BSA as above prior to use. Reaction and control tubes were incubated at 37° C. for 2 hr. Then mixtures were dialyzed against 5 mM EDTA for 5 hr and then against TC-PBS overnight at 4° C.

sCD4 was also treated to remove all oligosaccharides with a combination of Endoglycosidase F (New England Nuclear, Boston, Mass.) and N-glycosidase F (BEM, Indianapolis, Ind.). As above, all glassware and pipet tips were precoated with BSA. To a volume of 1 ml in 50 mM sodium phosphate (pH 7.0), there was mixed 50 microliters of sCD4 mix and 195 microliter enzyme mix. The control in which oligosaccharides were not removed contained 195 microliters 100 mM sodium phosphate, 25 mM EDTA, 50% glycerol in place of the enzyme mix. sCD4 mix was made by mixing 20 microliters of sCD4 with 110 microliters of 1 mg/ml BSA.

One rat was injected with the substantially deglycosylated sCD4 and another with the control sCD4 treated in parallel. Blood samples were taken at intervals and radioactivity was determined. The results are summarized in Table 5. It appears that the sCD4 polypeptide is cleared from the bloodstream somewhat more quickly than the corresponding intact glycoprotein molecule. These results suggest that clearance by the kidney, degradation and excretion in the urine is greater for the substantially deglycosylated sCD4 than for control glycosylated sCD4.

TABLE 1

Distribution of [$^{125}$I]-sCD4 in Liver and Blood Samples

| Rat Number | Time Post-Injection (min) | Input Counts (cpm) | % Input Counts Associated with Liver | % Input Counts in 1 ml Blood | Material Injected |
|---|---|---|---|---|---|
| R1 | 5 | 98,976 | 27.2% | 2.2% | sCD4 |
| R2 | 5 | 113,076 | 26.1% | 2.3% | |
| R4 | 10 | 125,480 | 12.3% | 4.0% | sCD4 plus Asialo-Fetuin |
| R5 | 10 | 126,053 | 19.8% | 2.7% | sCD4 plus Fetuin |

TABLE 2

Distribution of [$^{125}$I]-Asialo-sCD4 in Liver and Blood Samples

| Rat Number | Time Post-Injection (min) | Input Radio-activity (cpm) | % Input Radioactivity Associated with Liver | % Input Counts in 1 ml Blood | Material Injected |
|---|---|---|---|---|---|
| R11 | 10 | 124,954 | 61.8% | 0.6% | Asialo-sCD4 |
| R14 | 10 | 129,942 | 49.1% | 0.6% | Asialo-sCD4 |

TABLE 3

Distribution of [$^{125}$I]-sCD4 in Liver and Blood for Asialo-sCD4 with Intact and with Oxidized Galactose Residues

| Rat Number | Time Post-Injection (min) | Input Counts (cpm) | % Input Counts Associated with Liver | % Input Counts in 1 ml Blood | Material Injected |
|---|---|---|---|---|---|
| R26 | 10 | 141,621 | 64.6% | 0.64% | Asialo-sCD4 |
| R27 | 20 | 140,393 | 54.3% | 0.48% | |
| R25 | 20 | 102,695 | 23.3% | 2.6% | |
| R28 | 120 | 144,118 | 17.8% | 1.9% | GO/HPO-treated |
| R23 | 360 | 204,864 | 14.5% | 1.6% | Asialo-sCD4 |
| R29 | 1080 | 138,563 | 10.5% | 0.2% | |

TABLE 4

| | sCD4 Excretion Into Bile | |
|---|---|---|
| Time After Injection | R3 (sCD4) | R28 (GO/HPO-Asialo-sCD4) |
| 15 min | 1476 | 536 |
| 30 min | 6397 | 772 |
| 45 min | 8624 | 1094 |
| 60 min | 7611 | 1183 |
| 75 min | 6629 | 1038 |
| 90 min | 4719 | 928 |
| 105 min | 3716 | 884 |
| 120 min | 2980 | 760 |
| Total Bile: | 42152 (38% input) | 7195 (5% input) |
| Total Bile & Liver: | 48963 | 34774 |
| Total Input Counts: | 111,638 | 144,118 |
| Approximate Percent of Input Counts Associated with Bile and Liver | 40–45% | 24% |

TABLE 5

Effect of Deglycosylation of sCD4
(Endoglycosidase F + N-glycosidase F-treated Asialo-sCD4)
on Distribution of [$^{125}$I]-sCD4 in Liver and Blood

| Rat Number | Time Post-Injection (min) | Total Input Counts (cpm) | % Input Counts Associated with Liver | % Input Counts in 1 ml Blood | % Input Count in Urine & Bladder | Material Injected |
|---|---|---|---|---|---|---|
| R32 | 5 | 127,613 | ND* | 1.3% | ND | Deglycosylated sCD4 |
|  | 15 |  | ND | 0.81 | ND |  |
|  | 30 |  | ND | 0.75 | ND |  |
|  | 60 |  | ND | 0.53 | ND |  |
|  | 90 |  | ND | 0.44 | ND |  |
|  | 120 |  | 6.3% | 0.23 | 25.4% |  |
| R33 | 5 | 111,190 | ND | 2.0% | ND | sCD4 |
|  | 15 |  | ND | 1.13% | ND |  |
|  | 30 |  | 13.3% | 0.82% | 0.1% |  |

*ND = Not Determined

We claim:

1. A therapeutic composition comprising a concentration of oxidized galactose asialo-sCD4 effective for binding to HIV when administered to a patient and a pharmaceutically acceptable carrier.

2. The therapeutic composition of claim 1, wherein said oxidized galactose asialo-sCD4 has a human plasma half-life which is greater than about 24 hours.

3. The therapeutic composition of claim 1, wherein said modified sCD4 has been treated such that sufficient sialic acid residues have been removed to expose at least two galactose residues.

4. The therapeutic composition of claim 1, wherein said oxidized galactose asialo-sCD4 is produced by treating sCD4 such that terminal sialic acid residues are substantially removed, yielding asialo-sCD4, and wherein said asialo-sCD4 has been treated with galactose oxidase and horseradish peroxidase.

5. A method for increasing the half-life of sCD4 in circulation in a mammal, comprising the steps of
treating said sCD4 to remove terminal sialic acid residues to produce an asialo-sCD4,
oxidizing any galactose residues of said asialo-sCD4 to produce an oxidized galactose asialo-sCD4, and
administering said oxidized galactose asialo-sCD4 to a circulatory system of a mammal,
whereby removal of said oxidized asialo-sCD4 by the galactose receptors of said mammal's liver is inhibited.

6. The method of claim 5 wherein said asialo-sCD4 contains at least two exposed galactose residues.

7. The method of claim 5 wherein said sialic acid residues are removed using neuraminidase.

8. The method of claim 5 wherein said sCD4 is oxidized using galactose oxidase and horseradish peroxidase.

* * * * *